(12) United States Patent
Guan et al.

(10) Patent No.: US 12,738,383 B2
(45) Date of Patent: Sep. 15, 2026

(54) TELEHEALTH TERMINAL

(71) Applicant: Caregility Corporation, Wall Township, NJ (US)

(72) Inventors: Bin Guan, Wall Township, NJ (US); Simon Lowe, Wall Township, NJ (US); David Walter Galas, Wall Township, NJ (US)

(73) Assignee: CAREGILITY CORPORATION, Wall Township, NJ (US)

( * ) Notice: Subject to any disclaimer, the term of this patent is extended or adjusted under 35 U.S.C. 154(b) by 0 days.

(21) Appl. No.: 18/807,331

(22) Filed: Aug. 16, 2024

(65) Prior Publication Data

US 2025/0062041 A1 Feb. 20, 2025

Related U.S. Application Data

(60) Provisional application No. 63/520,265, filed on Aug. 17, 2023.

(51) Int. Cl.

| | |
|---|---|
| ***G16H 80/00*** | (2018.01) |
| ***G06F 8/65*** | (2018.01) |
| ***H04N 23/695*** | (2023.01) |

(52) U.S. Cl.

CPC ............... *G16H 80/00* (2018.01); *G06F 8/65* (2013.01); *H04N 23/695* (2023.01)

(58) Field of Classification Search

CPC .......... G16H 80/00; G16H 40/67; G06F 8/65; H04N 23/695; H04N 7/142; H04N 7/15

See application file for complete search history.

(56) References Cited

U.S. PATENT DOCUMENTS

| | | | | |
|---|---|---|---|---|
| 10,440,327 | B1 | 10/2019 | Bytyqi | |
| 2008/0259274 | A1* | 10/2008 | Chinnock | A61B 3/14 351/206 |
| 2010/0026817 | A1* | 2/2010 | Ryan | H04N 7/147 704/E11.001 |
| 2018/0226158 | A1* | 8/2018 | Fish | A61B 5/0022 |

(Continued)

OTHER PUBLICATIONS

International Search Report and Written Opinion for PCT/US2024/042769, dated Jan. 23, 2025, 17 pages.

(Continued)

*Primary Examiner* — Robert W Morgan
*Assistant Examiner* — Liza Tony Kanaan
(74) *Attorney, Agent, or Firm* — RANKIN, HILL & CLARK LLP

(57) ABSTRACT

A telehealth terminal includes at least one processer configured to process signals and perform computing and arithmetic functions, a first camera in electrical communication with the at least one processor, the first camera being configured to pan, tilt, and zoom to capture an environment around the telehealth terminal, and a second camera in electrical communication with the at least one processor, the second camera being spaced from the first camera. The terminal also includes at least one microphone in electrical communication with the at least one processor; and at least one speaker in electrical communication with the at least one processor, wherein the at least one processor provides communication between a first user that operates the telehealth terminal and a second user that is remote from the telehealth terminal.

16 Claims, 5 Drawing Sheets

(56) References Cited

U.S. PATENT DOCUMENTS

| | | | | |
|---|---|---|---|---|
| 2019/0046056 | A1* | 2/2019 | Khachaturian | A61B 5/0816 |
| 2020/0066414 | A1* | 2/2020 | Neff | H04L 12/1818 |
| 2020/0265961 | A1* | 8/2020 | Celmins | H04N 23/45 |
| 2021/0149206 | A1* | 5/2021 | Tiffin | G03B 30/00 |
| 2021/0374391 | A1* | 12/2021 | Jorasch | G06V 40/19 |

OTHER PUBLICATIONS

Communication Relating to the Results of the Partial International Search for PCT/US2024/042769, dated Nov. 27, 2024, 8 pages.

* cited by examiner

TELEHEALTH TERMINAL

BACKGROUND

Healthcare facilities often require advanced technological solutions to improve patient care, streamline workflows, and enhance communication between separate groups of healthcare professionals as well as with their patients. However, these facilities currently lack devices that can provide enhanced features to address the specific needs of demanding healthcare environments. Notably, there is an unmet need for an efficient, inviting, and user-friendly device that enhances healthcare operations while ensuring patient privacy and data security.

SUMMARY

A telehealth terminal can be used for a variety of critical medical workflows in healthcare facilities. The terminal is an Access Point of Care, which means that it is optimized to be managed and operated as a part of a software suite which provides device management, monitoring, and a platform for facilitating all calls and workflow related streams. The terminal can be paired with a display for provisioning and viewing the remote call participants and related content. Further, the terminal can be installed on a wall or cart that will be appropriately located for its participant's workflow.

The terminal provides both outstanding video quality with dual cameras that can include IR light for night vision, and well as outstanding audio quality with its microphone array, built-in speakers, and digital audio processing. The aesthetic and compact size of the enclosure, along with simple installation allow for usage in a wide range of medical rooms ranging including ICUs, acute care rooms, consultation rooms, and examination rooms.

According to an aspect, a telehealth terminal includes at least one processer configured to process signals and perform computing and arithmetic functions, a first camera in electrical communication with the at least one processor, the first camera being configured to pan, tilt, and zoom to capture an environment around the telehealth terminal, and a second camera in electrical communication with the at least one processor, the second camera being spaced from the first camera. The terminal also includes at least one microphone in electrical communication with the at least one processor; and at least one speaker in electrical communication with the at least one processor, wherein the at least one processor provides communication between a first user that operates the telehealth terminal and a second user that is remote from the telehealth terminal.

DETAILED DESCRIPTION

It should, of course, be understood that the description and drawings herein are merely illustrative and that various modifications and changes can be made in the structures disclosed without departing from the present disclosure. The terminology used herein is for the purpose of describing particular embodiments only and is not intended to be limiting of the invention. As used herein, the term "and/or" includes any and all combinations of one or more of the associated listed items. As used herein, the singular forms "a," "an" and "the" are intended to include the plural forms as well as the singular forms, unless the context clearly indicates otherwise.

Figure 1:
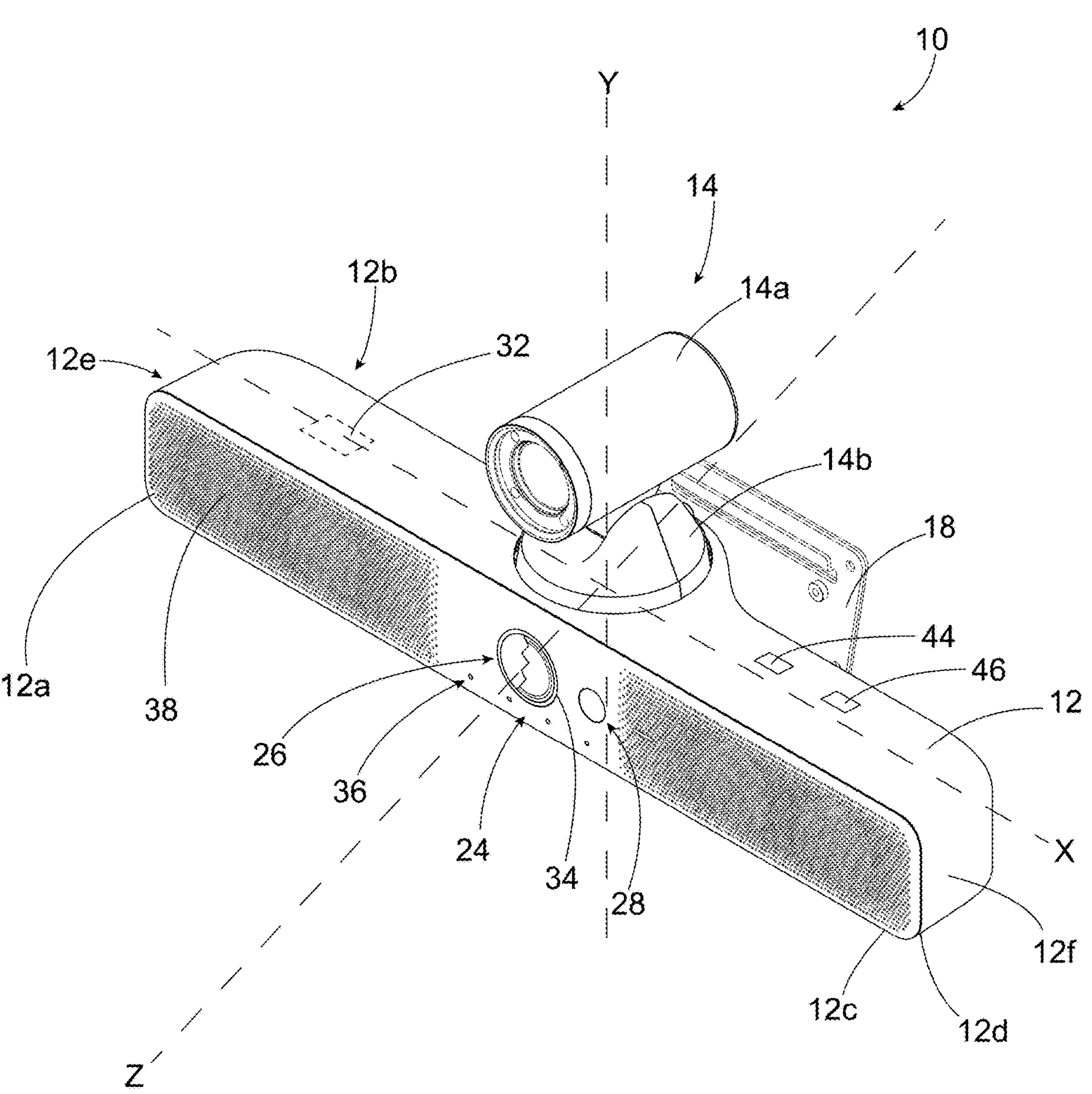
FIG. 1 is a top front right side isometric view of a telehealth terminal.
Figure 2:
FIG. 2 is a bottom rear left side isometric view of the telehealth terminal.
Figure 2:
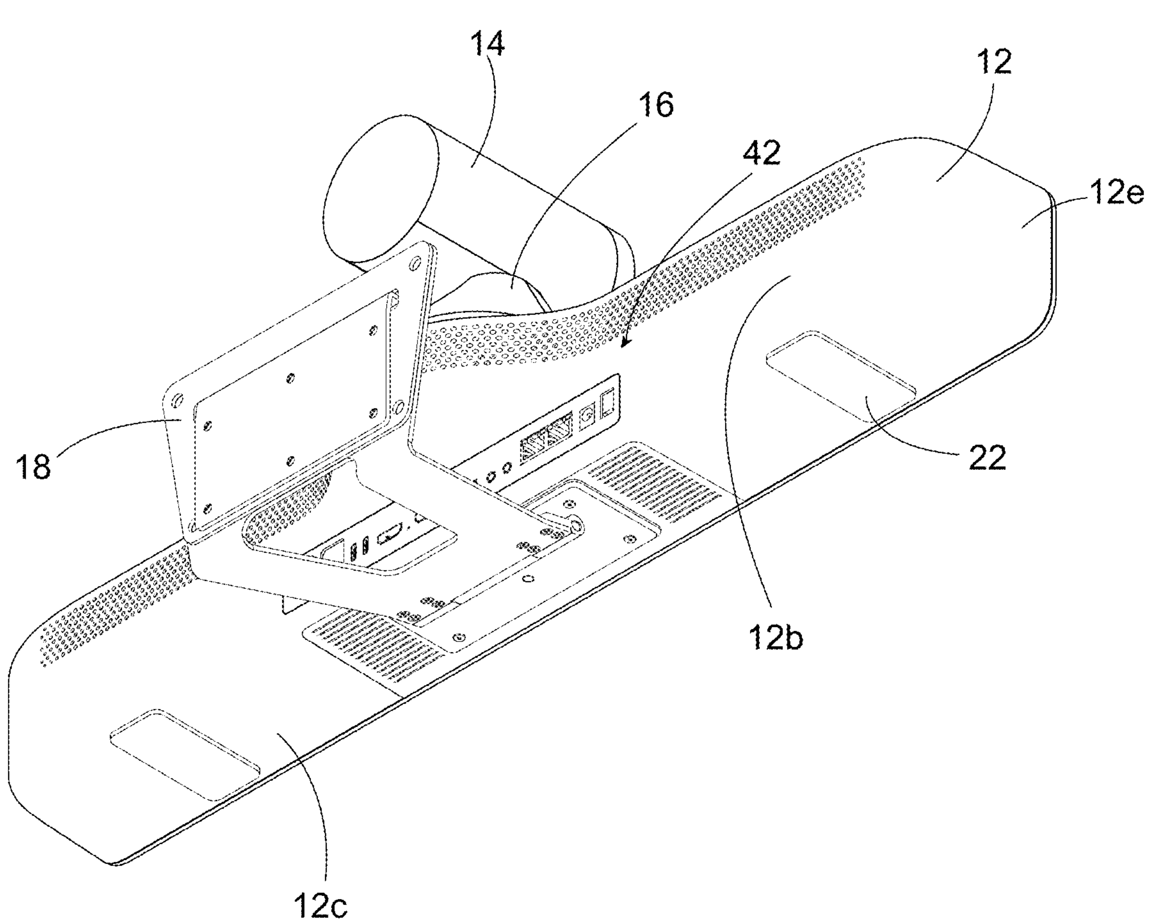

FIG. 1 illustrates a telehealth terminal 10 (hereinafter terminal 10). With reference to FIGS. 1 and 2, the terminal 10 can include a housing 12, a first camera 14 that can include a main body 14*a* and a pan and tilt mount 14*b*, a mounting bracket 18, and feet 22.

The housing 12 of the terminal 10 can include a second camera 24, a privacy cover 26, an IR illuminator 28, a processor 32, an LED light ring 34, at least one microphone 36, at least one speaker 38, and at least one port 42. The at least one microphone 36 can include, for example, six microphones, the at least one speaker 38 can include, for example, four speakers, and the at least one port 42 can include, for example, a plurality of ports.

The housing 12 can have a generally rectangular shape including a front face 12*a*, a rear face 12*b*, a bottom face 12*c*, a top face 12*d*, a first side face 12*e*, and a second side face 12*f*. The front face 12*a* can face the first user 1 (FIG. 3) and the rear face 12*b* can face in an opposite direction as the front face 12*a*. Further, the bottom face 12*c* and the top face 12*d* can face in opposite directions as one another.

The housing 12 can extend in a first axis X to define a width of the terminal 10 and a second axis Z to define a depth of the terminal 10. Further, the terminal 10 can also define a third axis Y that orthogonally extends from the first axis X and the second axis Z so as to define a height of the terminal 10.

As such, the housing 12 can contain the at least one processor 32 (hereinafter processor 32), the second camera 24, the at least one microphone 36, and the at least one speaker 38 therewithin. By having the components disposed within the housing 12, the terminal 10 is easily portable and compact. The front face 12*a* of the housing 12 can extend between the bottom face 12*c* of the housing 12 and the top face 12*d* of the housing 12. The second camera 24 and the at least one microphone 36 can be disposed on the front face 12*a* of the housing 12. This placement ensures that quality audio and video of the first user 1 are captured.

The housing 12 can be constructed of plastic and/or other materials that provide sufficient strength and rigidity. The front face 12*a* can define a number of holes to receive the microphones 36, the speakers 38, and also allow for audio communication therethrough. Further, the housing 12 can have a variety of ventilation perforations to allow passive ventilation for cooling.

As mentioned hereinbefore, the terminal 10 can include two high-resolution cameras strategically positioned to capture different room perspectives. The first camera 14 and the second camera 24 utilize advanced image sensors and lenses to produce clear and detailed visuals. Additionally, the incorporation of night vision technology ensures optimal image quality even in low-light conditions.

The first camera 14 can include an infrared cut filter that is configured to operate when the IR illuminator 28 is in operation. For reference, the second camera 24 can also include an infrared cut filter without departing from the scope of this disclosure. Such features allow for monitoring of a patient (i.e., first user 1) even when room lighting is non-existent or dimmed. Thus, the patient's health is improved when a restful sleep is possible due to the dimmed lighting.

The first camera 14 can be in electrical communication with the processor 32 and be configured to pan, tilt, and zoom to capture an environment 13 (FIG. 3) around the terminal 10. The first camera 14 can have a 58.5-degree horizontal viewing angle which will be generally used to capture a wide variety of room shots, often moving and zooming in to capture specific bookmarked detail images. The pan and tilt mount 14*b* of the first camera 14 can be disposed between the camera body 14*a* and the top face 12*d* along the third axis Y. Such an arrangement allows for a compact terminal 10 that can be easily moved.

Further, the first camera 14 can also have zoom capability. For example, the first camera 14 could be a 20× optical plus 2× digital zoom for capturing greater detail and wider motion of 170 degree pan and 15 degrees tilt. This allows the first camera 14 to capture the environment 13 around the terminal 10.

As will be appreciated, the environment 13 could include a variety of spaces without departing from the scope of this disclosure. For example, the environment 13 could include a patient's hospital room, an examination room in a hospital or other care facility, or an operating room. Thus, the first camera 14 can provide great control and flexibility for zooming in on a variety of targets in the room.

The second camera 24 can be in electrical communication with the processor 32 and be spaced from the first camera 14. The second camera 24 can be a static camera with a 110-degree horizontal viewing angle generally used to capture full images of the room (i.e., environment 13). The second camera 24 can also have zoom capability.

For example, the second camera 24 can be a 5× digital zoom to allow limited zoom to provide some additional detail and also include panning and tilt control to allow the user to have slight adjustments of the room view. The second camera 24 can be vertically spaced from the first camera 14 such that the second camera 24 is disposed between the at least one microphone 36 and the first camera 14 along the third axis Y in a plane defined by the first axis X and the third axis Y. Because of this close placement of the second camera 24 and the microphone 36 together, audio is more effectively captured, as the patient will naturally direct their speech toward where they looking into the second camera 24.

The LED light ring 34 can annularly surround the second camera 24 and be in electrical communication with the processor 32. Further, the LED light ring 34 can be configured to indicate an operating status of the terminal 10. For example, the LED light ring 34 could be activated to glow a certain color (e.g., white, blue, red, green, yellow, and/or purple) to indicate that the terminal 10 is in use (i.e., in a call). Thus, the LED light 34 provides a quick and easily identifiable means of whether the terminal 10 is in operation, so that the user 1 can take the necessary privacy actions.

The first camera 14 and the second camera 24 can each include IR capability. The IR capability can be shared or each camera can utilize a unique IR array. The IR illuminator 28 array can illuminate with 850 nm to provide IR light for low light night vision, which can be utilized by the first camera 14 and the second camera 24. The IR illuminator 28 can be disposed on the front face 12*a* so as to be between the at least one microphone 36 and the top face 12*d* along an axis that that is parallel to the third axis Y in a plane defined by the first axis X and the third axis Y.

The placement of the IR illuminator 28 in the location as described ensures that the user 1 is properly illuminated for purposes of the cameras 14, 24. As will be appreciated, the IR illuminator 28 can be in electrical communication with the processor 32 and be disposed within the housing 12 to provide IR illumination for at least the second camera 24 to capture images in the environment 13 in low-light situations.

As previously mentioned, the terminal 10 can include the mechanical privacy cover 26 for the second camera 24 that can be controlled by the processor 32 and opened when the second camera 24 is active and closed when the second camera 24 is not in a call. Thus, the privacy cover 26 can provide a physical barrier when closed and also visually indicate that the second camera 24 is inactive and protecting patients' privacy.

This can provide the patient with a sense of comfort that they are not being monitored by the second camera 24. When opened, the second camera 24 is ready for use, facilitating communication and monitoring. By having a mechanical device to cover the second camera 24, the first user 1 can be confident that their privacy is maintained when the privacy cover 26 blocks the second camera 24. Thus, the first user 1 does not have to worry that hacking has occurred and video access is still being provided by the camera even though it was not authorized.

Thus, the mechanical privacy cover 26 selectively limits the second camera 24 from viewing the environment 13 around the terminal 10 so as to provide a privacy option for the first user 1. The mechanical privacy cover 26 defines a first state that permits the second camera 24 to view the environment 13 around the terminal 10 to facilitate communication and monitoring of the first user 1 by the second user 2 and a second state that prevents the second camera 24 from viewing the environment 13 around the terminal 10 to provide privacy to the first user 1, and wherein the privacy cover 26 is in the second state whenever the terminal 10 is not in communication with the second user 2.

Figure 3:
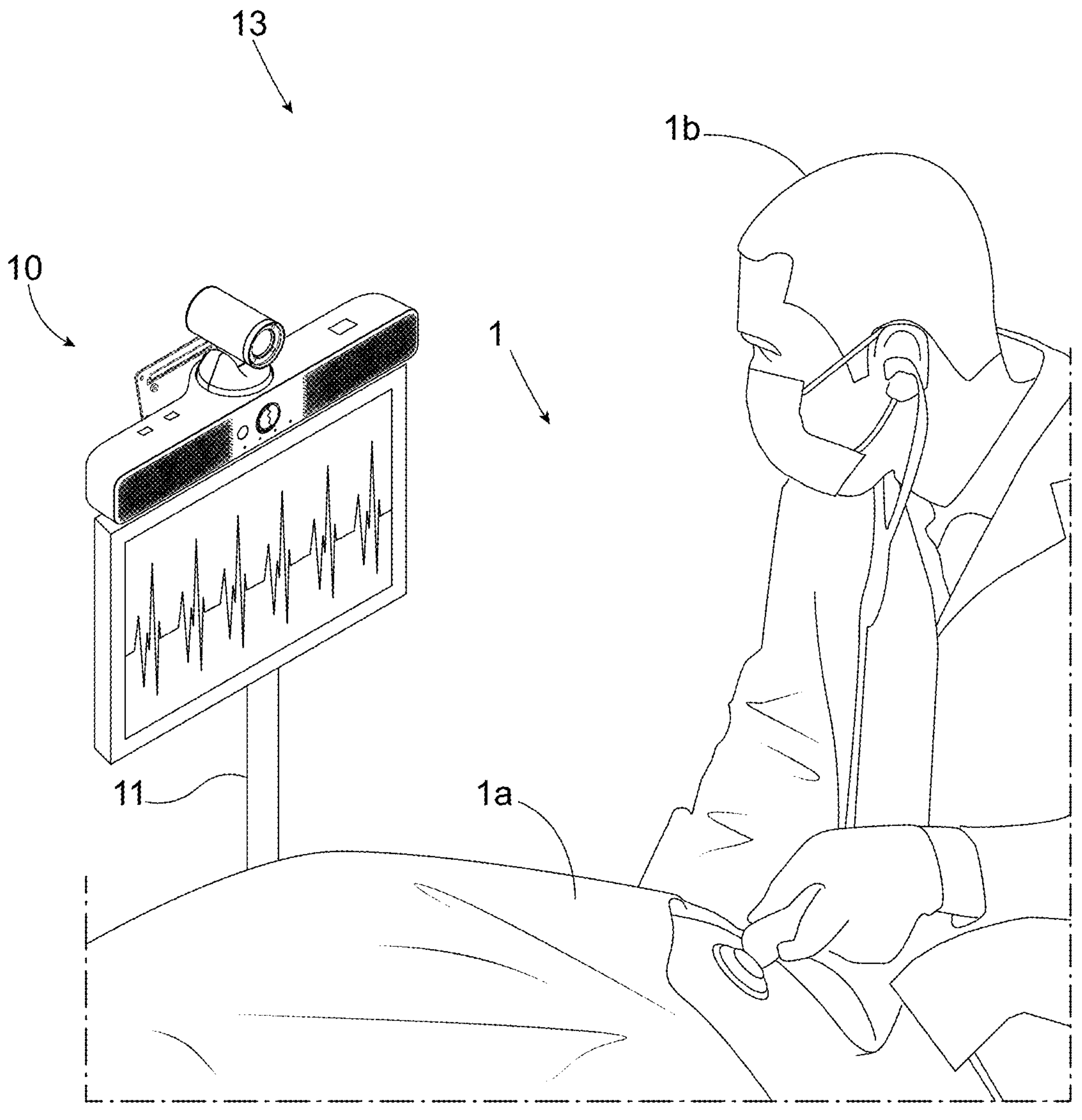
FIG. 3 is a schematic view of the telehealth terminal in use.
Figure 4:
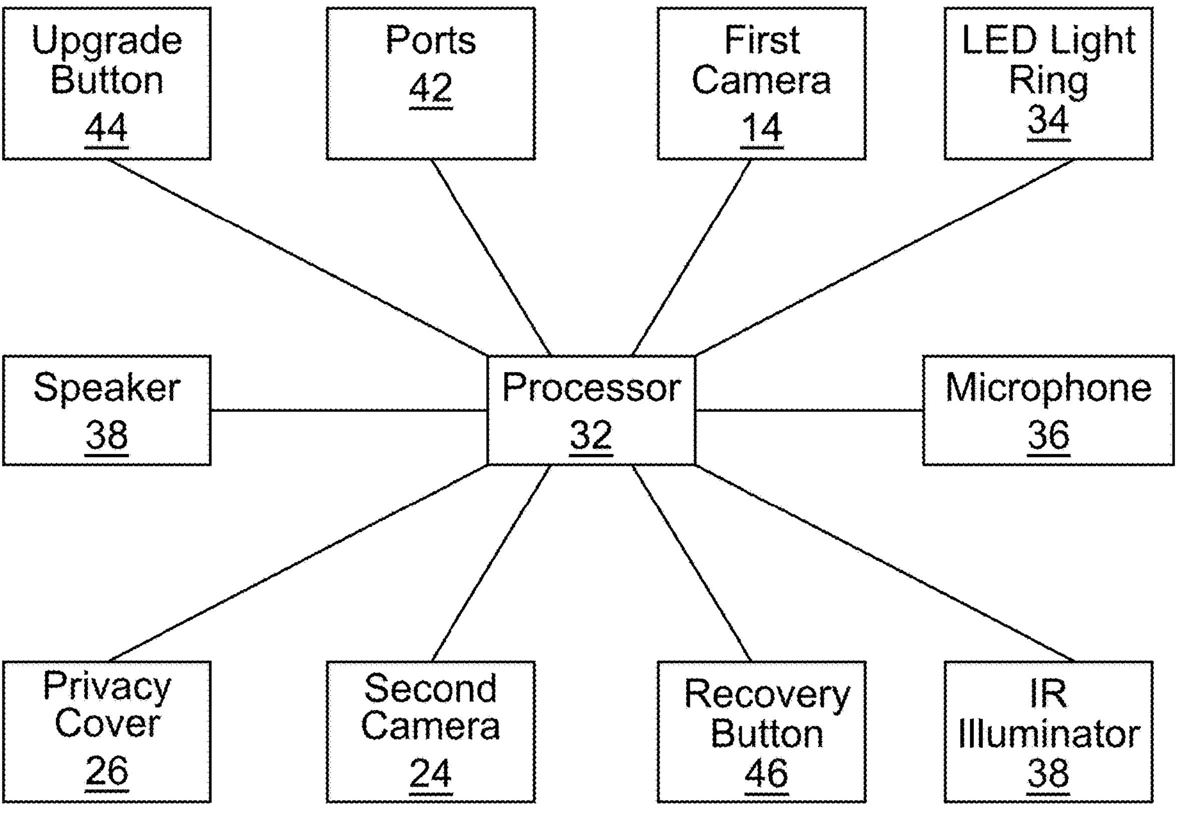
FIG. 4 is a schematic view illustrating connections between various components of the telehealth terminal.
Figure 5:
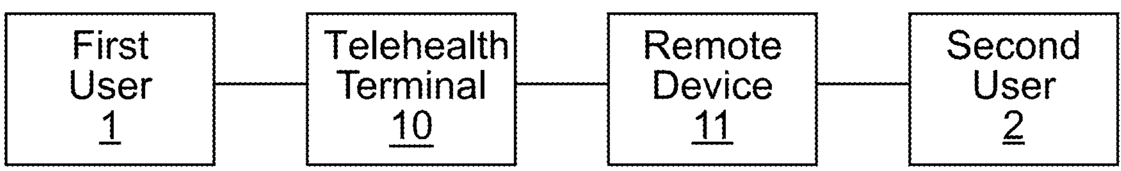
FIG. 5 is a schematic view illustrating connections between a first user of the telehealth terminal and a second user.

With reference to FIGS. 3 and 5, it will be appreciated that the first user 1 could include a variety of individuals without departing from the scope of this disclosure. For example, as shown in FIG. 3, the first user 1 could include a patient 1*a* and/or a healthcare provider 1*b* that is providing aid/assistance to the patient 1*a*. Further, the second user 2 could also include a variety of individuals. For example, the second user 2 could be a remote medical provider and/or another interested party that is either providing consultation or merely observing the status of the first user 1.

With continued attention to FIGS. 3 and 5, remote is understood to be a location that is spaced from and distinct from the environment 13. Remote could include a location that is in the same building as the environment 13, but a different room. Alternatively, remote could mean in a different city than the environment 13. Finally, the remote device 11 could be another terminal 10 or different device, without departing from the scope of this disclosure. The different device could be a laptop or desktop computer, with or without cameras.

FIG. 1 illustrates the privacy cover 26 midway between the first state and the second state with a jagged line illustrating a section of the privacy cover 26 so that it is visible. As will be appreciated, when the privacy cover 26 in the first state, the privacy cover 26 would not be viewable in the figure. Conversely, when in the second state, the lens of the second camera 24 would not be viewable in the figure. Thus, the privacy cover 26 is shown in a partially deployed state in FIG. 1.

Also, to enhance patient privacy, the first camera 14 can be controlled to face away from the front face 12*a* when the terminal 10 is not in a call or when the camera deactivated.

For example, the processor 32 can be configured to instruct the first camera 14 to rotate about the third axis Y to an angular position that is opposite to an angular position that the second camera 24 faces when the privacy cover 26 is in the second state.

Because of the first camera 14, the second camera 24, and the IR illuminator 28, high-quality images and videos can be captured from multiple viewing angles. Additionally, the incorporation of night vision technology enables clear imaging even in low-light environments, ensuring accurate monitoring and documentation without impacting the patient's rest.

Further, because of the multi-camera and multi-microphone 36 array, there can be simultaneous streaming of multiple video and audio feeds, enabling different healthcare professionals to engage in real-time collaboration across different workflows at a single time. This feature enhances communication, facilitates remote consultations, scalability, and optimizes decision-making processes within the healthcare setting.

The at least one microphone 36 can be in electrical communication with the processor 32 and be capable of capturing clear audio from distances of over twenty feet. This feature enables healthcare professionals to participate in discussions and provide instructions from a distance, enhancing patient care and operational efficiency.

As will be appreciated, the microphones 36 can include configurable advanced audio processing such as AGC (Auto Gain Control), NS (Noise Suppression), and EC (Echo Canceller). Further, the microphones 36 can allow healthcare professionals to effectively communicate with full duplex audio with colleagues, patients, and even monitor any sounds from medical devices without compromising clarity or compromising patient safety. The processing can eliminate unwanted room ambient sounds as well.

The microphones 36 can be disposed in an array that is parallel to the first axis X. Further, at least one of the plurality of microphones 36 can be disposed on the front face 12*a* so as to be between the second camera 24 and a junction of the front face 12*a* and the bottom face 12*c*. Such an arrangement ensures that the audio is effectively captured, as the user 1 will be focused on the second camera 24, and thus, their voice will be projected toward the microphones 36.

The at least one speaker 38 can be in electrical communication with the processor 32. Accordingly, the processor 32 can provide communication between a first user 1 (FIGS. 3 and 5) that operates the terminal 10 and a second user 2 (FIG. 5) that is remote from the terminal 10. The speakers 38 can operate at a frequency of from 100 Hz to 16 kHz and ensure that the audio from the remote participants, alert notifications, and new call doorbell tones to be monitored at an elevated level.

The plurality of speakers 38 can be disposed in an array that is parallel to the first axis X in a plane defined by the first axis X and the third axis Y. This layout of the speakers 38 helps to provide an improved experience for the user 1. Notably, the user 1 will more likely hear any audio broadcast over the speakers 38, since they will be focused on the second camera 24.

The plurality of ports 42 can be in electrical communication with the processor 32 and the at least one processor 32 can be configured to transmit and receive data from the plurality of ports 42 to facilitate multiple workflows. The ports 42 allow for integration with room components, displays peripherals, etc. It will be appreciated that there are a variety of connectors that facilitate the connectivity of different devices to facilitate multiple workflows.

For example, the ports 42 can include USB Type A connectors and USB Type C connectors that can provide connectivity for medical peripherals, technician support, remote vLert Button, and flexibility for future expansion. The ports 42 can also include an HDMI output to connect to the display to show call and setup content from the terminal 10 itself or the pass through an input source and an HDMI input source to use the built-in HDMI switcher function in case there is a customer workflow that requires an additional device input.

Additionally, the ports 42 can optionally include RJ45 network sources for wired network connectivity. The RJ45 port could also optionally be used for supplying POE (Power Over Internet). The ports 42 could also include a 3.5 mm audio connector for auxiliary audio inputs and outputs devices to provide future expansion.

The terminal 10 can also include an upgrade button 44 in electrical communication with the processor 32 to put the terminal 10 in an update mode when its OS/firmware needs to be updated. Accordingly, the at least one processor 32 can be configured to update firmware of the terminal 10 when the upgrade button 44 is depressed.

The terminal 10 can also include a recovery button 46 that will return the terminal 10 to its basic factory reset. The recovery button 46 can be in electrical communication with the at least one processor 32 and the at least one processor 32 configured to change all current settings of the terminal 10 to a configuration to match original settings of the terminal 10.

As illustrated, the upgrade button 44 and the recovery button 46 are disposed on the top face 12*d* of the console 12. However, the upgrade button 44 and the recovery button 46 can be located in a variety of places on the terminal 10 without departing from the scope of disclosure. Further, the upgrade button 44 and the recovery button 46 can be recessed to prevent inadvertent actuation.

As shown in FIG. 3, the terminal 10 can be wall mounted above an HD display 11 with the bracket 18 or by other means without departing from the scope of this disclosure. The HD display 11 can show its output for provisioning and setup, and it will also show a room ID, and show the remote site during a call. This HD display 11 can be an IPC or local infotainment/hospitality display displaying local facility information, patient entertainment as provided by the local site provider. The terminal 10 can also be cart mounted, so that it can be moved between locations. Alternatively, the terminal 10 can also be table/desk mounted with the feet 22.

The processor 32 is configured to process signals and perform computing and arithmetic functions and is capable of concurrently handling multiple video and audio streams to enable healthcare professionals to engage in real-time collaboration across different workflows, such as remote consultations, medical procedures, inclusion of select medical peripheral integrations and patient monitoring. The processor 32 can also be configured to provide Bluetooth connectivity in the environment 13 to allow diagnostic equipment to connect to the terminal 10. As such, additional medical peripherals can be connected to the terminal 10 and subsequently viewed by the second user 2. This allows for additional data to be captured in the environment 13 for improved patient care.

The processor 32 can include a CPU, a GPU, an NPU, and memory. Memory may include volatile memory and/or nonvolatile memory. Non-volatile memory may include, for example, ROM (read only memory), PROM (programmable read only memory), EPROM (erasable PROM), and EEPROM (electrically erasable PROM). Volatile memory may include, for example, RAM (random access memory), synchronous RAM (SRAM), dynamic RAM (DRAM), synchronous DRAM (SDRAM), double data rate SDRAM (DDRSDRAM), and direct RAM bus RAM (DRRAM). The memory may store an operating system that controls or allocates resources of a computing device.

The processor 32 allows each customer entity to select their own operating system depending on their own workflow, security, and functional preferences. It will be understood that "processor 32" as used herein, processes signals and performs general computing and arithmetic functions. Signals processed by the processor 32 may include digital signals, data signals, computer instructions, processor instructions, messages, a bit, a bit stream, that may be received, transmitted and/or detected.

Generally, the processor 32 may be a variety of various processors including multiple single and multicore processors and co-processors and other multiple single and multicore processor 32 and co-processor 32 architectures. Thus, the processor 32 is configured to concurrently process and transmit multiple video and audio streams to the second user 2. Thus, efficiency of patient care is improved. Finally, the processor 32 may include logic circuitry to execute actions and/or algorithms.

The processor 32 serves a variety of purposes including: running the operating system, audio and video signal processing, power management, wifi/Bluetooth communication, and control of the various components connected thereto. For example, the processor 32 can be connected to and communicates with the first camera 14, the second camera 24, the LED light ring 34, the microphones 36, the speakers 38, the port 42, the upgrade button 44, and the recovery button 46.

This communication may occur across any type of wired or wireless system and/or network having any type of configuration, for example, a local area network (LAN), a personal area network (PAN), a wireless personal area network (WPAN), a wireless network (WAN), a wide area network (WAN), a metropolitan area network (MAN), a virtual private network (VPN), a cellular network, a token ring network, a point-to-point network, an ad hoc network, a mobile ad hoc network, among others.

This communication may utilize any type of wired, wireless, or network communication protocol including, but not limited to, Ethernet (e.g., IEEE 802.3), WiFi (e.g., IEEE 802.11), communications access for land mobiles (CALM), WiMax, Bluetooth, Zigbee, ultra-wideband (UWAB), multiple-input and multiple-output (MIMO), telecommunications and/or cellular network communication (e.g., SMS, MMS, 3G, 4G, LTE, 5G, GSM, CDMA, WAVE), satellite, dedicated short range communication (DSRC), among others.

The terminal 10 has a wide variety of uses. For example, the terminal 10 could be used for telemedicine and remote consultations and healthcare professionals could engage in real-time consultations with remote colleagues, specialists, or patients, allowing for timely diagnosis and treatment planning. Further, the terminal 10 could be used for medical procedures. For example, the terminal 10 could facilitate live streaming and documentation of medical procedures, enabling real-time collaboration and educational opportunities for medical students and residents. The terminal 10 could also be used for patient monitoring.

Notably, the terminal 10 can be used for remote patient monitoring, ensuring accurate and continuous observation of vital signs, patient conditions, and activity. The terminal 10 can also be used for training and education, thereby allowing medical professionals to share knowledge and expertise across separate locations.

The terminal 10 may also be used for translation services to enhance communication between healthcare professionals and patients of different languages and also for communication to all patient family members. The additional streams will allow the integration of different medical peripherals to provide additional workflows, as well as services with AI.

A telehealth terminal has been described above in particularity. Modifications and alternations will occur to those upon reading and understanding the preceding detail description. The invention, however, is not limited to only the embodiment described above. Instead, the invention is broadly defined by the appended claims and the equivalents thereof.

The invention claimed is:

1. A telehealth terminal, comprising:

at least one processer configured to process signals and perform computing and arithmetic functions;

a first camera in electrical communication with the at least one processor, the first camera being configured to pan, tilt, and zoom to capture an environment around the telehealth terminal;

a second camera in electrical communication with the at least one processor, the second camera being spaced from the first camera;

at least one microphone in electrical communication with the at least one processor;

at least one speaker in electrical communication with the at least one processor, wherein the at least one processor provides communication between a first user that operates the telehealth terminal and a second user that is remote from the telehealth terminal;

a mechanical privacy cover that selectively limits the second camera from viewing the environment around the telehealth terminal so as to provide a privacy option for the first user, wherein the mechanical privacy cover defines a first state that permits the second camera to view the environment around the telehealth terminal to facilitate communication and monitoring of the first user by the second user and a second state that prevents the second camera from viewing the environment around the telehealth terminal to provide privacy to the first user, and wherein the privacy cover is in the second state whenever the telehealth terminal is not in communication with the second user; and a housing extending in a first axis to define a width of the telehealth terminal and a second axis to define a depth of the telehealth terminal, wherein the telehealth terminal also defines a third axis that orthogonally extends from the first axis and the second axis so as to define a height of the telehealth terminal, wherein the housing includes a front face that faces the first user, a rear face that faces in an opposite direction as the front face, a bottom face, and a top face that faces in an opposite direction as the bottom face, and wherein the at least one processer is configured to instruct the first camera to rotate about the third axis to an angular position that is opposite to an angular position that the second camera faces when the privacy cover is in the second state.

2. The telehealth terminal of claim 1, wherein the housing contains the at least one processor, the second camera, the at least one microphone, and the at least one speaker therewithin, the front face of the housing extending between the bottom face of the housing and the top face of the housing, and wherein the second camera and the at least one microphone are disposed on the front face of the housing.

3. The telehealth terminal of claim 2, wherein the at least one microphone includes a plurality of microphones that are disposed in an array that is parallel to the first axis, and wherein at least one of the plurality of microphones is disposed on the front face so as to be between the second camera and a junction of the front face and the bottom face.

4. The telehealth terminal of claim 2, wherein the at least one speaker includes a plurality of speakers that are disposed in an array that is parallel to the first axis in a plane defined by the first axis and the third axis.

5. The telehealth terminal of claim 1, further comprising an infrared illuminator in electrical communication with the at least one processor, the infrared illuminator disposed within the housing and configured to provide infrared illumination for at least the second camera to capture images in the environment in low-light situations.

6. The telehealth terminal of claim 5, wherein the infrared illuminator also provides infrared illumination for the first camera.

7. The telehealth terminal of claim 5, wherein the first camera includes an infrared cut filter that is configured to operate when the infrared illuminator is in operation and the first camera is configured to zoom at a rate of up to 20 times to capture the environment around the telehealth terminal.

8. The telehealth terminal of claim 5, wherein the infrared illuminator is disposed on the front face so as to be between the at least one microphone and the top face along an axis that that is parallel to the third axis in a plane defined by the first axis and the third axis.

9. The telehealth terminal of claim 1, the first camera including a camera body and a pan and tilt mount, wherein the pan and tilt mount is disposed between the camera body and the top face along the third axis.

10. The telehealth terminal of claim 1, wherein the second camera is vertically spaced from the first camera such that the second camera is disposed between the at least one microphone and the first camera along the third axis in a plane defined by the first axis and the third axis.

11. The telehealth terminal of claim 1, further comprising a plurality of ports in electrical communication with the at least one processer, the at least one processor configured to transmit and receive data from the plurality of ports to facilitate multiple workflows.

12. The telehealth terminal of claim 1, wherein the at least one processor is configured to concurrently process and transmit multiple video and audio streams to the second user.

13. The telehealth terminal of claim 1, wherein the at least one processor is configured to provide Bluetooth connectivity in the environment to allow diagnostic equipment to connect to the telehealth terminal.

14. The telehealth terminal of claim 1, further comprising a light emitting diode light ring that annularly surrounds the second camera, wherein the light emitting diode light ring is in electrical communication with the at least one processor and configured to indicate an operating status of the terminal.

15. The telehealth terminal of claim 1, further comprising an upgrade button in electrical communication with the at least one processer, the at least one processor configured to update firmware of the terminal when the upgrade button is depressed.

16. The telehealth terminal of claim 1, further comprising a recovery button in electrical communication with the at least one processer, the at least one processor configured to change all current settings of the terminal to a configuration to match original settings of the terminal.

* * * * *